United States Patent
Mayumi et al.

(10) Patent No.: US 7,189,824 B2
(45) Date of Patent: *Mar. 13, 2007

(54) TUMOR VESSEL ENDOTHELIAL CELL-BINDING MONOCLONAL ANTIBODIES

(75) Inventors: Tadanori Mayumi, Hyogo (JP); Shinsaku Nakagawa, Osaka (JP); Yasuo Tsutsumi, Osaka (JP); Iwao Ohizumi, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 212 days.

This patent is subject to a terminal disclaimer.

(21) Appl. No.: 10/012,271

(22) Filed: Nov. 8, 2001

(65) Prior Publication Data

US 2002/0081305 A1    Jun. 27, 2002

Related U.S. Application Data

(63) Continuation of application No. 09/125,162, filed as application No. PCT/JP97/00387 on Feb. 17, 1997, now Pat. No. 6,440,733.

(30) Foreign Application Priority Data

Feb. 15, 1996 (JP) ............................... 1996/27931

(51) Int. Cl.
C07K 16/00 (2006.01)
C12P 21/08 (2006.01)
A61K 39/395 (2006.01)
G01N 33/574 (2006.01)
C12P 21/04 (2006.01)

(52) U.S. Cl. ............................... 530/388.1; 530/387.3; 530/388.8; 530/388.85; 530/391.1; 530/391.7; 424/133.1; 424/141.1; 424/155.1; 424/156.1; 424/181.1; 435/7.23; 435/69.6; 435/70.21

(58) Field of Classification Search ................ 435/330, 435/334, 344, 70.2, 70.21, 449, 7.23, 69.6; 530/388.2, 388.8, 389.7, 391.7, 387.1, 387.3, 530/388.1, 388.23, 388.73, 389.6, 388.85, 530/391.1; 424/174.1, 133.1, 141.1, 155.1, 424/156.1, 181.1
See application file for complete search history.

(56) References Cited

U.S. PATENT DOCUMENTS 5,489,525 A * 2/1996 Pastan
5,530,101 A * 6/1996 Queen et al.
5,951,982 A * 9/1999 Zoller et al.

FOREIGN PATENT DOCUMENTS

WO   WO-94/12631   6/1994
WO   WO-95/33771   12/1995

OTHER PUBLICATIONS

William E. Paul. Fundamental Immunology, Ch 8, pp. 242, 1993.*
Taniguchi et al. International Journal of Cancer, 86(6):799-805, 2000.*
Harlow et al. Antibodies, A Laboratory Manual, Chapter 5, pp. 141-142, 1988.*
Ohe et al. British Journal of Cancer, 67:939-944, 1993.*
Chiba et al., Cancer Research (1987) 47:1815-1819.
Connolly et al., Journal of Clinical Investigation (1989) 84(5):1470-1478.
Duerst et al., Exp. Hematol. (1991) 19:863-867.
Farr et al., J. Exp. Med. (1992) 176:1477-1482.
Iyer et al., Exp. Hematol. (1990) 18:384-389.
Kasai et al., JNCI (1981) 67(2):417-422.
Minami et al., Int. J. Cancer (1979) 23:358-365.
Ohizumi et al., Biochemical and Biophysical Research Communications (1997) 236:493-496.
Supplementary European Search Report for EP 97 90 2678, mailed on Oct. 28, 2004, 6 pages.
Taniguchi et al., Biochemical and Biophysical Research Communications (2000) 269:671-675.
Tsunoda et al., British Journal of Cancer (1999) 81(7):1155-1161.
Utoguchi et al., Jpn. J. Cancer Res. (1995) 86:193-201.
Wetterwald et al., Bone (1996) 18(2):125-132.
Brooks, et al. "Antiintegrin αvβ3 Blocks Human Breast Cancer Growth and Angiogenesis in Human Skin" J. Clin. Invest. 96:1815-1822 (1995).
Bruland, et al. "Expression and Characteristics of a Novel Human Osteosarcoma-Associated Cell Surface Antigen" Cancer Res. 48:5302-5309 (1988).
Burrows, et al. "Eradication of Large Solid Tumors in Mice with an Immunotoxin Directed Against Tumor Vasculature" Proc. Natl. Acad. Sci. USA 90:8996-9000 (1993).
Clark, et al. "The Identification of Proliferation and Tumour-induced Proteins in Human Endothelial Cells: A Possible Target for Tumour Therapy" Electrophoresis 12:500-508 (1991).

(Continued)

Primary Examiner—Sheela J. Huff
Assistant Examiner—David J. Blanchard
(74) Attorney, Agent, or Firm—Morrison & Foerster LLP

(57) ABSTRACT

A monoclonal antibody which recognizes an antigen of a molecular weight of 40 kD or 80 kD on the surface of tumor vessel endothelial cells, hybridomas producing the monoclonal antibody, pharmaceutical agents comprising the monoclonal antibody, as well as pharmaceutical or diagnostic agents comprising a conjugate of the monoclonal antibody and another conjugating molecule.

17 Claims, 5 Drawing Sheets

OTHER PUBLICATIONS

Duzhang, et al. "Generation of Monoclonal Antibodies Directed Against Organ-Specific Endothelial Cell Surface Determinants" J. Histochem. Cytochem. 39(8):1137-1142, (1991).

Fox, et al. "CD44 and Cancer Screening" The Lancet 342:548-549, (1993).

Mark, et al. "The Identification of Proliferation and Tumour-Induced Proteins in Human Endothelial Cells: A Possible Target for Tumour Therapy" Electrophoresis 12:500-508 (1991).

Naoki, et al. "Isolation and Properties of Tumor-Derived Endothelial Cells from Rat KMT-17 Fibrosarcoma" Jpn. J. Cancer Res. 86:193-201 (1995).

Rettig, et al. "Identification of Endosialin, A Cell Surface Glycoprotein of Vascular Endothelial Cells in Human Cancer" Proc. Natl. Sci. USA 89:10832-10836 (1992).

Wang, et al. Int. "A Monoclonal Antibody Detects Heterogeneity in Vascular Endothelium of Tumours and Normal Tissues" J. Cancer 54:363-370 (1993).

Wettrwald, et al. "Characterization and Cloning of the E11 Antigen, a Marker Expressed by Rat Osteoblasts and Osteocytes" Bone 18(2):125-132 (1996).

Osteoblasts and Osteocytes Bone 18(2):125-132 (1996).

* cited by examiner

Days after transplantation of tumor cells

TUMOR VESSEL ENDOTHELIAL CELL-BINDING MONOCLONAL ANTIBODIES

CROSS-REFERENCE TO RELATED APPLICATION

This application is a continuation application of application Ser. No. 09/125,162, filed Aug. 17, 1998, now U.S. Pat. No. 6,440,733, the contents of which is incorporated herein by reference, which is a national phase filing of PCT/JP97/00387, filed Feb. 17, 1997.

TECHNICAL FIELD

The present invention relates to monoclonal antibodies recognizing antigens expressed on the surface of tumor vessel endothelial cells, hybridomas producing said antibodies, pharmaceutical agents comprising said antibodies, as well as pharmaceutical or diagnostic agents comprising a conjugate of one of said antibodies and another conjugating molecule.

BACKGROUND ART

Currently known anticancer agents include anticancer DDS agents using antibodies against tumor cells as a targeting carrier. However, this type of anticancer agent has the disadvantage that tumor interstitial pressure or other barriers hinder permeation of the agent to significantly lower the performance of drug delivery to the target. Moreover, a particular antibody could not be used as a common targeting carrier for various types of tumors, because of heterogeneity of antigens on the surface of tumor cells.

However, there may be expressed common specific molecules in tumor tissue vessel endothelial cells (TEC) irrespective of the type of cancer because tumor vessels have many common characteristics such as enhanced permeation function. Targeting therapy directed to tumor vessels is expected to effectively achieve the advantages of anticancer DDS agents without concern about barriers to transfer to tissues, and therefore, monoclonal antibodies which are specific for vessel endothelial cells, particularly vessel endothelial cells existing in tumor tissues (tumor vessel endothelial cells) have been developed.

Up to the present, markers widely recognizing vessel endothelial cells such as CD31, CD36, Ulex europaeus-I agglutinin (UEA-1) and markers generally expressed inactivated large vessel endothelial cells such as von Willebrand factor (vWF), ICAM-1 (CD54), E-selectin have been known.

On the other hand, tumor vessel endothelial cells are postulated to express specific antigens which are not expressed in normal tissues as described above, and various antibodies recognizing tumor vessel endothelial cells have been reported up to the present, among which some examples are listed below:

E-9 antibody (Wang, J. M. et al., Int. J. Cancer (1993) 54, 363);
anti-FB5 (endosialin) antibody (Rettig, W. J. Pro. Natl. Sci. USA (1992) 89, 10832);
H4/18 antibody (Cotran, R. S. et al., J. Exp. Med. (1986) 164, 661);
Q BEND/10 antibody (Ramani, P. et al., Histopathology (1990) 17, 237);
EN4/EN3 antibody (Schlingemann, R. O. et al., Amer. J. Pathol. (1991) 138, 1335);
BMA120 antibody (Schlingemann, R. O. et al., Amer. J. Pathol. (1991) 138, 1335);
EN7/44 antibody (Hagemeier, H. H. et al., Int. J. Cancer (1986) 38, 481);
PAL-E antibody (Schlingemann, R. O. et al., Amer. J. Pathol. (1991) 138, 1335);
HEC-1 antibody (Gougos, A. et al., J. Immunol. (1988) 141, 1934);
TEC4 and TEC11 antibodies (Thorpe, P. E. et al., Am. Assoc. Cancer Res. (abstract) (1994) 35, 379).

However, antigens recognized by these antibodies are also expressed in normal endothelial cells or other cell species, though in a minor amount, and nothing has been reported about antitumor effects of these antibodies, leading to a demand for development of antibodies which are more suitable for the therapy of solid cancers targeting tumor vessel endothelial cells.

CD 44 is a known antigenic protein existing on the surface of lymphocytes or the like (J. Immunol., 142, 2045–2051, Mar. 15, 1989), and monoclonal antibodies against CD44 have been reported (JP Laid-open Publication (Kokai) No. 508309/93; WO94/12631; and WO95/33771). However, these antibodies against CD44 have not been reported to recognize antigens on the surface of tumor vessel endothelial cells, and CD44 has not been reported to exist on the surface of tumor vessel endothelial cells, either, prior to the priority date of the present application.

DISCLOSURE OF THE INVENTION

An object of the present invention is to provide novel monoclonal antibodies recognizing antigens on the surface of tumor vessel endothelial cells.

Another object of the present invention is to provide novel monoclonal antibodies recognizing antigens specifically existing on the surface of tumor vessel endothelial cells.

Still another object of the present invention is to provide hybridomas producing novel monoclonal antibodies recognizing antigens on the surface of tumor vessel endothelial cells.

Still another object of the present invention is to provide pharmaceutical agents comprising novel monoclonal antibodies recognizing antigens on the surface of tumor vessel endothelial cells.

Still another object of the present invention is to provide pharmaceutical or diagnostic agents comprising a conjugate of a monoclonal antibody recognizing an antigen on the surface of tumor vessel endothelial cells and a conjugating molecule for treating or diagnosing tumor-associated conditions.

As a result of careful studies to solve the above problems, the present inventors succeeded in obtaining monoclonal antibodies recognizing antigens existing on the surface of tumor vessel endothelial cells, analyzing the distribution of the obtained antibodies in organs and the antigenic proteins, and confirming that said monoclonal antibodies administered alone or in combination with other drugs to tumor-transplanted rats show inhibitory effects on solid cancers, and thus accomplished the present invention.

Accordingly, the present invention provides, in the broadest sense, monoclonal antibodies recognizing antigens on the surface of tumor vessel endothelial cells, hybridomas producing said monoclonal antibodies, pharmaceutical agents comprising said monoclonal antibodies, as well as pharmaceutical or diagnostic agents comprising a conjugate of one of said monoclonal antibodies and another conjugating molecule.

According to a first aspect of the present invention, a monoclonal antibody which recognizes an antigen of a molecular weight of 40 kD or 80 kD on the surface of tumor vessel endothelial cells is provided.

According to the present invention, said monoclonal antibody wherein the affinity for tumor vessel endothelial cells is comparable to or higher than the affinity for normal vessel endothelial cells when the affinity for tumor vessel endothelial cells and normal vessel endothelial cells both immobilized is measured by ELISA is provided.

Also according to the present invention, said monoclonal antibody wherein the reactivity to tumor tissues is comparable to or higher than the reactivity to the liver and kidney when the reactivity to tissue samples of tumor, liver and kidney of rats is measured by immunohistochemical staining is provided.

Also according to the present invention, said monoclonal antibody wherein the level in tumor tissues is comparable to or higher than the level in blood and the level in the liver, lung, spleen, small intestine and muscle is comparable to or lower than the level in blood when the antibody is administered to rats bearing tumors is provided.

Also according to the present invention, said monoclonal antibody produced by hybridomas of a single clone obtained by the steps of immunizing an animal with cell membrane vesicles prepared from tumor vessel endothelial cells from rat KMT-17 solid cancer, isolating antibody-producing cells from said animal, fusing said antibody-producing cells to melanoma cells to prepare hybridomas, and screening the thus-obtained hybridomas, is provided.

Also according to the present invention, said monoclonal antibody wherein said immunization procedure further comprises passively immunizing said animal with an antiserum against cell membrane vesicles prepared from normal vessel endothelial cells before immunizing said animal with cell membrane vesicles prepared from tumor vessel endothelial cells is provided.

Also according to the present invention, said monoclonal antibody produced by hybridomas bearing the accession number FERM BP-5786 or FERM BP-5787 is provided.

Also according to the present invention, said monoclonal antibody having antitumor activity is provided.

According to a second aspect of the present invention, a hybridoma producing said monoclonal antibody according to the present invention is provided.

Particularly preferably, a hybridoma bearing the accession number FERM BP-5786 or FERM BP-5787 is provided according to the present invention.

According to a third aspect of the present invention, a pharmaceutical agent comprising said monoclonal antibody is provided.

Preferably, said pharmaceutical agent for the treatment of tumors is provided according to the present invention.

According to a fourth aspect of the present invention, a pharmaceutical or diagnostic agent comprising a conjugate of (a) said monoclonal antibody and (b) a conjugating molecule selected from the group consisting of anticancer chemotherapeutic agents, radioisotopes, proteinous toxins, lethal proteins or expression vectors carrying genes expressing them, enzymes, streptavidin is provided.

Preferably, said pharmaceutical or diagnostic agent for the treatment or diagnosis of tumors is provided.

THE BEST MODE FOR CARRYING OUT THE INVENTION

Figure 1:
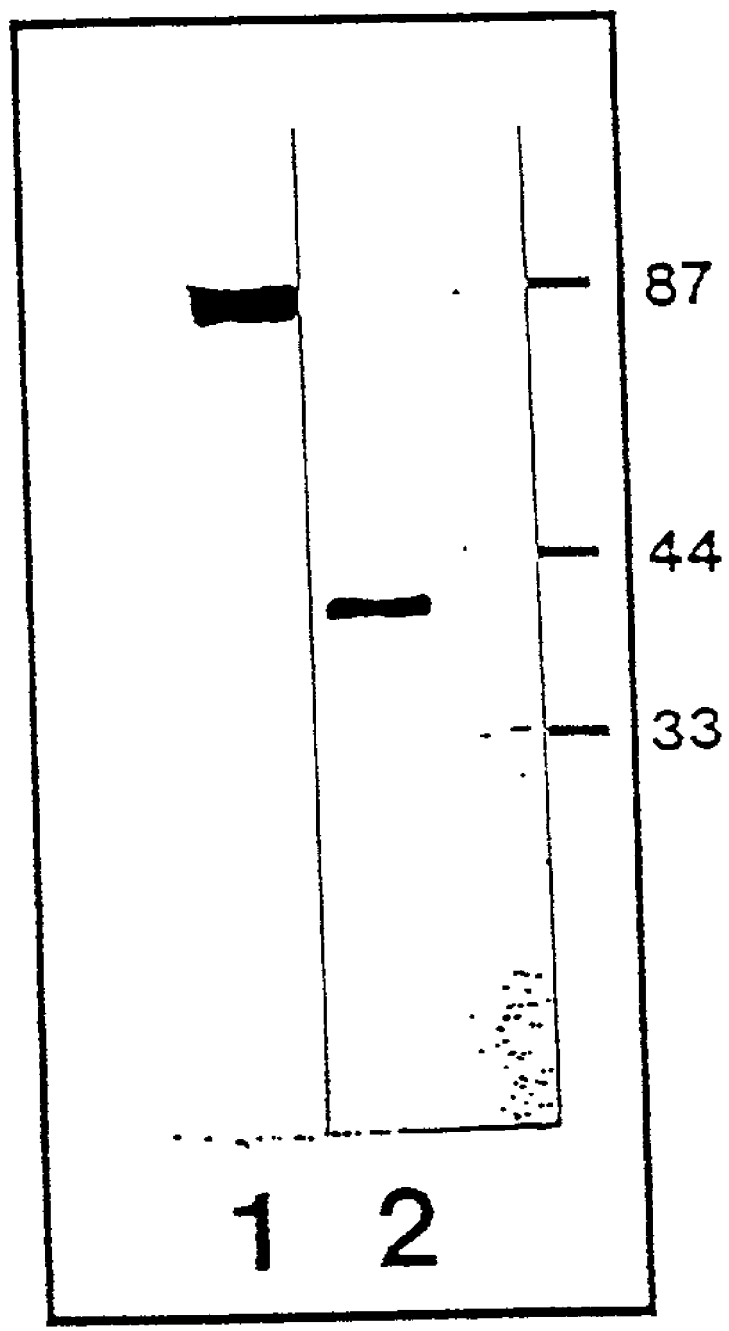
FIG. 1 is a photograph of Western blotting showing proteins recognized by TES23-3-10 (lane 1) or TES1-10-1 (lane 2).

A process for preparing a monoclonal antibody recognizing an antigen on the surface of tumor vessel endothelial cells according to the present invention will now be explained below.

As an immunogen for obtaining an antibody of the present invention, tumor vessel endothelial cells can be used. The sources and methods for isolating these cells are not particularly limited, but these cells may be generally isolated from samples which are expected to be rich in them.

An example of the method for isolating tumor vessel endothelial cells is described in Utoguchi et al., Jpn. J. Cancer Res. (1995) 86, 193–201, as will be used in the examples described below.

However, it is obvious that this is a mere example of the method for isolating tumor vessel endothelial cells, and may be modified in various ways to obtain a monoclonal antibody of the present invention.

Then, an animal is immunized with tumor vessel endothelial cells obtained by, for example, the above method, preferably by using membrane fractions isolated from said cells for the purpose of obtaining an antibody specific for an antigen existing on cell surfaces of tumor vessel endothelial cells.

Immunization may also be accomplished by intraperitoneally administering living cells ($10^6$ to $10^7$ cells) (without adjuvant) as an immunogen in place of cell membrane fractions. In this case, the final immunization involves intravenous administration of $10^6$ living cells.

Membrane fractions can be isolated by conventional procedures known to those skilled in the art. For example, culture cells are treated with DMEM containing 100 mM paraformaldehyde, 2 mM dithiothreitol, 1 mM $CaCl_2$ and 0.5 mM $MgCl_2$ at 37° C. overnight, then the culture medium is centrifuged at 10 g and the resulting supernatant is centrifuged at 30,000 g for 30 minutes at 4° C. to give pellets containing suitable cell membrane vesicles (Scott, R. E. Science (1976) 194, 743–745).

For the purpose of obtaining an antibody specific for tumor vessel endothelial cells, the animal is preferably preimmunized with an antiserum obtained by immunizing a mouse or the like with membrane fractions prepared from isolated normal vessel endothelial cells (including various antibodies against antigens on the surface of normal vessel endothelial cells), prior to immunization with membrane fractions from tumor vessel endothelial cells. Such preimmunization of the subject animal with an antiserum against normal vessel endothelial cells is also called as "masking" and regarded as one of effective means for efficiently obtaining an intended antibody (i.e. an antibody against an antigen specifically expressed on the surface of tumor vessel endothelial cells in case of the present invention).

The species of animal to be used to obtain a monoclonal antibody of the present invention is not specifically limited, but should preferably be an animal with a high antibody-producing ability preferably selected in view of the compatibility with melanoma cells used for cell fusion. Typical species include mouse, rat, rabbit, hamster, preferably mouse, especially BALB/c mouse.

As described above, the animal is immunized with membrane fractions of tumor vessel endothelial cells preferably after preliminary injection of an antiserum against normal vessel endothelial cells (passive immunization). The time, frequency, dose, manner, etc. of this immunization can be appropriately chosen dependent on the species, conditions or other factors of the animal to be immunized within the scope of the knowledge of those skilled in the art.

The frequency of administration is generally 1 to 15 times, preferably 3 to 5 times, and the time when booster challenges take place can also be appropriately determined by those skilled in the art.

The total dosage is generally 10 to 2000 μg, preferably 50 to 700 μg in an amount expressed as protein when an antigen is administered, and this dosage may be administered at a time or divided into multiple doses, as described above.

If needed, membrane fractions prepared from tumor vessel endothelial cells may be administered after emulsified with an appropriate immunoadjuvant such as complete Freund's adjuvant or incomplete Freund's adjuvant.

The manner of injecting an immunogen includes, but not specifically limited to, subcutaneous, intraperitoneal, intrasplenic, intracutaneous, intramuscular, intralymphonodal or intravenous injection.

After said immunization, antibody-producing cells for preparing hybridomas are isolated from the immunized animal. Antibody-producing cells producing monoclonal antibodies of the present invention are B-cells, which are known to circulate in the body but also accumulate in some organs such as the spleen. Therefore, antibody-producing cells are preferably prepared with the spleen extracted from the immunized animal, though other organs rich in B-cells may also be used.

Then, thus obtained antibody-producing cells are immortalized by fusing them to melanoma cells.

Any cell fusion technique known to those skilled in the art may be used.

Cell fusion is generally accomplished by incubating antibody-producing cells with melanoma cells of an infinitely proliferative cell line deficient in hypoxanthine-guanine phosphoribosyl transferase (HGPRT) in a medium containing a fusion promoting agent.

Any known type of melanoma cells may be used, including, but not limited to, mouse melanoma cells such as P3X63Ag8U.1, Sp2/0-Ag14, and rat melanoma cells such as YB2/0, Y3/Ag1.2.3. Melanoma cells should preferably be selected in view of the compatibility with antibody-producing cells.

Suitable fusion promoting agents include chemical compounds such as polyethylene glycol or cell fusion-mediating viruses such as Sendai virus, and auxiliaries for enhancing fusion efficiency may be further added.

Cell fusion is performed by mixing said antibody-producing cells and melanoma cells in a cell culture medium in an appropriate ratio of antibody-producing cells to melanoma cells, generally 1:1 to 20:1, preferably 2:1 to 10:1, followed by addition of a fusion promoting agent. Then, addition of appropriate culture media and removal of supernatants are repeated to form hybridomas.

Then, only fused cells are selected by cultivation in a hypoxanthine aminopterin thymidine (HAT) medium. The cultivation of cells in the HAT medium may be done for a period enough to kill cells other than hybridomas, normally for several days to several weeks.

Means for immortalizing antibody-producing cells are not limited to cell fusion (preparation of hybridomas) but may be other known techniques.

For example, immortalization may be accomplished by transformation with Epstein-Barr viruses (EBV) when human B-lymphocytes are used as antibody-producing cells.

Then, thus obtained hybridomas are screened to obtain a single clone producing an antibody recognizing an antigen on the surface of tumor vessel endothelial cells. Suitable cloning techniques for obtaining a single clone are known to those skilled in the art, such as limiting dilution analysis, soft agar technique.

Suitable screening techniques for obtaining hybridomas producing an intended antibody are also known to those skilled in the art, including various techniques for detecting an antibody such as ELISA, plaque hybridization, agglutination reaction, RIA, immunohistochemical staining.

Screening may be performed stepwise by including, for example, primary screening and secondary screening, in view of improvement of operation efficiency or other effect. For example, a possible protocol includes primary screening based on ELISA and secondary screening based on immunohistochemical staining, as described in the examples below.

Thus obtained cell line producing an intended antibody can be subcultured in ordinary media and can be stored for a long period in, for example, liquid nitrogen.

In order to obtain a monoclonal antibody recognizing an antigen on the surface of tumor vessel endothelia according to the present invention from hybridomas prepared as described above, the following two methods may be used.

A first method involves cultivating said hybridomas for a predetermined period in an appropriate medium, and isolating and purifying monoclonal antibodies produced by the hybridomas from the supernatant of cultures by using affinity column chromatography, for example.

A second method involves intraperitoneally injecting said hybridomas into a compatible mammal (i.e. having an isogene or semi-isogene) such as mouse, and then isolating and purifying monoclonal antibodies produced by the hybridomas from sera or ascites of the animal after a predetermined period.

Suitable monoclonal antibodies are not limited to those derived from hybridomas produced by cell fusion of antibody-producing cells obtained by immunization with an antigen, but may also be produced by gene recombination technique involving introducing an appropriate vector carrying a cloned antibody gene into a known cell line such as COS, CHO (for example, see Vandamme, A-M. et al., Eur. J. Biochem., 192, 767–775, 1990).

Thus obtained monoclonal antibodies of the present invention have characteristics as described in the examples below. Specifically, monoclonal antibodies as characterized below are provided according to the present invention.

One of characteristics of monoclonal antibodies of the present invention is that the affinity for tumor vessel endothelial cells is comparable to or higher than the affinity for normal vessel endothelial cells, e.g. in a ratio of the affinity for tumor vessel endothelial cells to the affinity for normal vessel endothelial cells of 1 or more, for example, 1.9, or 20.0 or more, for example, 22.7, or 200 or more, when the affinity for tumor vessel endothelial cells and normal vessel endothelial cells both immobilized is measured by ELISA.

Another characteristic of monoclonal antibodies of the present invention is that the reactivity to tumor tissues is comparable to or higher than the reactivity to the liver and kidney, when the reactivity to tissue samples of tumor, liver and kidney of rats is measured by immunohistochemical staining.

Still another characteristic of monoclonal antibodies of the present invention is that the level in tumor tissues is comparable to or higher than the level in blood, especially in a ratio of 4.0 or more, and the level in the liver, lung, spleen, small intestine and muscle is comparable to or lower than the level in blood, especially in a ratio of 0.5 or less, when the distribution in organs of rats bearing tumors to which a radiolabeled monoclonal antibody has been intravenously administered is determined by measuring radioactivity in each organ by a gamma counter.

CD44 (lymphocyte homing receptor) is recognized by TES23-3-10 and TES27-4-4 described in the examples below as examples of monoclonal antibodies recognizing an antigen of 80 kD according to the present invention. OTS-8 (a marker expressed in osteoblasts and osteocytes) is recognized by TES1-10-1, TES7-1-7, TES17-8-4, TES21-14-6 and TES26-7-3 described in the examples below as examples of monoclonal antibodies recognizing an antigen of 40 kD according to the present invention.

The 80 kD antigen recognized by TES23-3-10 and TES27-4-4 is derived from tumor vessel endothelial cells, but not collected from normal tissues or cancer cells. TES23-3-10 was found to be taken up into tumor vessel endothelial cells after binding to them, but no report has shown that existing anti-CD44 antibodies are taken up into cells. TES-23-3-10 was found to strongly stain tumor vessels by immunohistological staining of tumor tissues, but existing anti-CD44 antibodies weakly stain them.

Monoclonal antibodies recognizing antigens on the surface of tumor vessel endothelia according to the present invention are useful for diagnosing not only primary cancers but also localization of metastatic lesions by internally administering said antibodies labeled with a radioisotope or the like.

Monoclonal antibodies according to the present invention are also useful as pharmaceutical agents, especially for the treatment of tumors, because they show antitumor effects even when they are administered alone to tumors as shown in Example 4 below.

The antibodies TES23-3-10 and TES27-4-4 recognizing CD44 as described in the examples below show antitumor effects on proliferation of solid cancer cells which do not express CD44, as a result of targeting at tumor vessel endothelial cells.

Monoclonal antibodies used in the present invention are not limited to monoclonal antibodies produced by hybridomas, but more preferably should be artificially modified to lower heteroantigenecity to humans. For example, it is possible to use a chimeric antibody comprising variable regions of a monoclonal antibody of a non-human mammal such as mouse and constant regions of a human antibody, and such a chimeric antibody can be prepared by a known technique, especially gene recombination technique.

Reshaped human antibodies may also be used in the present invention. They are constructed by transplanting complementarity determining regions of an antibody of a non-human mammal such as mouse into complementarity determining regions of a human antibody, generally by a known gene recombination technique. Reshaped human antibodies which are useful in the present invention can be obtained by using such a known technique (for example, see International Publication No. WO92/19759).

If needed, an amino acid in a framework (FR) region of variable regions of reshaped human antibodies may be changed so that complementarity determining regions of the antibodies may form suitable antigen-binding sites (Sato et al., Cancer Res. (1993) 53, 1–6).

Conjugates of a monoclonal antibody of the present invention and another conjugating molecule may be applied for targeting therapy directed to tumor tissues. Specific examples of conjugating molecules that can be used particularly for the diagnosis or treatment of tumors are listed below.

(1) Low-molecular compounds represented by chemotherapeutic agents or antiproliferative compounds for vessel endothelial cells, such as neocarcinostatin, adriamycin, mitomycin C, etoposide, vinblastine, fumagillin derivatives;

(2) Labels for detecting the presence of an antibody, including radioisotopes such as $^{125}I$, $^{131}I$, $^{90}Y$, $^{186}Re$, 67CU, $^{212}Bi$, $^{211}At$ and $^{99m}Tc$;

(3) Proteinous toxins such as ricin, diphtheria toxin, Pseudomonas exotoxin A, pokeweed seed-derived anti-virus protein;

(4) Lethal proteins or expression vectors carrying genes expressing them, more specifically, TNF-α, INF-γ, Fas ligands or the like;

(5) Enzymes converting precursors such as chemotherapeutic agents into active forms, such as β-lactamase-labeled antibody+cephalosporin-bound adriamycin, alkaline phosphatase-labeled antibody+monophosphate-bound etoposide;

(6) Molecules having a specific affinity for a specific substance such as streptavidin (after it is fixed to tissues, a biotin-labeled drug is administered), more specifically streptavidin-labeled antibody +biotin-labeled anticancer chemotherapeutic agent or the like.

These molecules can be conjugated to an antibody by the following techniques. Anticancer chemotherapeutic agents, proteins or gene vectors may be conjugated by using a crosslinking agent such as SMCC (Batra, J. K. et al., Pro. Natl. Acad. Sci. USA (1992) 89, 5867), SPDP (Carlsson, J. et al., Biochem. J. (1978) 173, 723), SMPT (Thrope, P. E. et al., Cancer Res. (1987) 47, 5924–5931), 2IT (Thrope, P. E. et al., Cancer Res. (1987) 47, 5924–5931), or proteins may be conjugated as fusion proteins by genetic engineering (Bosslet, K. et al., Br, J. Cancer (1992) 65, 234). Radioisotopes can be conjugated to an antibody by the Iodogen method ($^{125}I$, $^{131}I$: see Example 2) or using a chelator such as RP1 ($^{99m}Tc$: Buist, M. R. et al., Cancer Res. (1993) 53, 5413).

Tumor vessel endothelium-specific antibodies of the present invention can be applied to diagnosis and treatment. For diagnosis, an antibody labeled with a radioisotope ($^{125}I$, $^{131}I$, $^{90}Y$, $^{186}Re$, $^{188}Re$, $^{67}Cu$, $^{212}Bi$, $^{211}At$, etc.) can be intravenously administered to cancer patients to know not only primary cancers but also localization of metastatic cancers non-aggressively and rapidly.

For application to treatment, an antibody to which is conjugated a molecule such as a drug can be intravenously administered to cancer patients to achieve targeting therapy at tumor tissues. The administration route is preferably parenteral via, for example, intravenous injection, intramuscular injection, intraperitoneal injection, subcutaneous injection for the purpose of systemic or local administration. Intravenous administration is the most preferred administration route because antigens localize at inner faces of vessels.

Antibodies of the present invention or said conjugates of an antibody and another molecule may be in the form of a pharmaceutical composition or a kit in combination with at least one pharmaceutically acceptable carrier or diluent.

The dosage to humans of pharmaceutical agents of the present invention, particularly for the treatment of tumors, depends on the condition and age of the patient or the manner of administration, but must be appropriately selected in a suitable amount. For example, an amount of about 1 to 1000 mg/patient divided into 4 or less doses can be chosen. Alternatively, a dosage of 1 to 10 mg/kg/week may be administered. However, the dosage of pharmaceutical agents of the present invention, particularly for the treatment of tumors, is not limited to the above ranges.

Pharmaceutical agents of the present invention, particularly for the treatment of tumors, can be formulated by conventional procedures (see Remington's Pharmaceutical Science, latest edition, Mark Publishing Company, Easton, US). For example, injectable formulations may be prepared by dissolving a purified antibody in a solvent such as physiological saline, buffer, glucose solution supplemented with an anti-adsorbent such as TWEEN™ 80, gelatin, human serum albumin (HAS), or may be lyophilized for reconstitution before use. Suitable excipients for lyophilization include sugar alcohols or sugars such as mannitol, glucose.

The following examples further illustrate the present invention without, however, limiting the same thereto.

EXAMPLES

Example 1

Preparation of Hybridomas Producing the Tumor Vessel Endothelial Monoclonal Antibodies TES1-10-1. TES7-1-7. TES17-8-4, TES21-14-6, TES23-3-10. TES26-7-3. TES27-4-4

According to the technique of Zhu, D. and Pauli, B. U., J. Histochem. Cytochem. (1991) 39, 1137–1142, monoclonal antibodies against tumor vessel endothelium-specific antigens were prepared by masking antigens expressed in normal vessel endothelial cells by administration of antisera.

Normal vessel endothelial cells were isolated from rat fat tissues and cultivated according to the technique of Madri, J. A. and Williams, S. K., J. Cell Biol. (1983) 97, 153–165. Then, the cells were treated with Dulbecco's modified Eagle's medium (DMEM) containing 100 mM paraformaldehyde, 2 mM dithiothreitol, 1 mM $CaCl_2$ and 0.5 mM $MgCl_2$ at 37° C. overnight to prepare cell membrane vesicles (Scott, R. E. Science (1976) 194, 743–745). An emulsion of 116 μg of the cell membrane vesicles in complete Freund's adjuvant was subcutaneously injected into BALB/c mice (Japan SLC). After 1, 2, 4 and 6 weeks, an emulsion of 86 μg of the cell membrane vesicles in incomplete Freund's adjuvant was subcutaneously injected. Three days after the final injection, blood was collected from the mice to obtain antisera against normal vessel endothelial cells.

Then, tumor vessel endothelial cells were isolated from rat KMT-17 solid cancer subcutaneously formed in WKAH/Hkm rats (Nippon SLC) and cultivated according to the technique of Utoguchi, N. et al., Jpn. J. Cancer Res. (1995) 86, 193–201, specifically by the following procedures.

At first, KMT-17 tumor cells ($3 \times 10.\text{sup}.5$ cells), which are transplantable fibrosarcoma cells induced by 3-methylcholanthrene in WKAH/Hkm rats, were transplanted into WKAH/Hkm rats, and the tumor was collected after it has reached a weight of 10–14 g. The collected tumor was placed in a balanced salt solution containing an antibiotic to remove peripheral and necrotic tissues, and then the remaining tumor tissues were minced with scissors or a razor. Thus minced tissues were digested with 0.75% collagenase, and the resulting cell suspension was passed through nylon mesh (300 μm) and washed twice in MEM containing 10% FCS by centrifugation. The precipitates were resuspended in MEM containing 10% FCS, and 2 ml of the cell suspension ($1.0.\text{times}. 10$ cells) was applied on the top of a 45% PERCOLL™ gradient (9 ml of PERCOLL™, 1 ml of $10.\text{times}.$ MEM, 10 ml of MEM containing 10% FCS) prepared by centrifugation at 20,000 g for 15 minutes in an angle rotor. The gradient tube was centrifuged at 1,500 g for 10 minutes in a swing rotor to continuously fractionate the suspension into fractions of 2 ml each from the top of the PERCOLL™ gradient. During this step, 11 fractions were obtained.

The 11 fractions of cells were washed twice with MEM to remove the PERCOLL™ solution, then the cells were resuspended in DMEM containing 10% FCS and 25 μg/ml of endothelial cell growth supplements and plated on culture plates. After growth of 24 hours, cells were washed with PBS to remove unattached cells.

The cell suspension of each fraction was washed twice with HBSS, then the cells were resuspended in borate buffer and sonicated.

Then, each fraction was analyzed for angiotensin converting enzyme (ACE) activity, protein content and the number of cells.

Cells from fractions showing relatively high ACE activity were grown on tissue culture plates, but it should be noted that such fractions contain a number of heterogeneous cells. Thus, unattached cells were washed off after growth of 24 hours to selectively grow only attached cells in view that endothelial cells are attached more rapidly than other cells. As a result, morphologically homogeneous cells were obtained and identified as endothelial cells derived from rat KMT-17 solid cancer by positive signals in Factor VIII staining.

Then, cell membrane vesicles were prepared in the same manner as for normal endothelial cells. Five minutes after intravenous injection of 100 μl of antisera against normal endothelial cells into BALB/c mice (Japan SLC), an emulsion of 174 μg of tumor vessel endothelial cell membrane vesicles in complete Freund's adjuvant was subcutaneously injected. After 4, 5 and 8 weeks, an emulsion of 97 μg of tumor vessel endothelial cell membrane vesicles in incomplete Freund's adjuvant was subcutaneously injected. Four-weeks afterthe final injection, a suspension of 358 μg of tumor vessel endothelial cell membrane vesicles in PBS was intraperitoneally injected to further enhance antibody-producing ability of the mice. After 3 day, the spleen was extracted from the mice, and the extracted splenic cells were fused to melanoma cells P3X63Ag8U.1 according to the technique of Harlow, E. and Lane, D. (Antibodies, a Laboratory Manual, Cold Spring Harbor (1988) 203).

Antibodies in the supernatant of hybridoma cultures were screened by ELISA (Posner, M. R. et al., J. Immunol. Methods (1982) 48, 23) using plates coated with tumor vessel endothelial cells or normal vessel endothelial cells. Isolated tumor vessel endothelial cells or normal vessel endothelial cells were dispensed into a 96-well plate (Falcon) in an amount of $2 \times 10^4$ cells per well and grown overnight. Confluent cells were washed twice with PBS and immobilized with PBS containing 0.1% glutaraldehyde at 4° C. for 10 minutes. Then, the plate was blocked with a 50 mM Tris-HCl (pH 8.1) solution containing 150mm NaCl, 1 mM $MgCl_2$, 0.05% TWEEN™ 20 , 0.02% $NaN_3$ and 1% BSA, and then incubated with the supernatant of hybridoma cultures at room temperature for 1 hour. Then, the plate was reacted with an alkaline phosphatase-labeled anti-mouse IgG goat antibody (Zymed) at room temperature for 1 hour, washed 5 times and reacted with a p-nitrophenyl phosphate substrate solution (Sigma) at room temperature for 1 hour.

The reaction was stopped with 2N sulfuric acid and the absorbance was measured by a microplate reader (Bio-Rad) at 405–620 nm (measured at 405 nm vs. reference wavelength of 620 nm). Clones which bind more strongly to tumor vessel endothelial cells than normal vessel endothelial cells were judged as positive. Positive hybridomas were cloned twice and the supernatant of these hybridoma cultures was used to assess the reactivity to tissue samples of rat KMT-17 tumor as well as rat liver and kidney by immunohistochemical staining.

The results are shown in the following Table 1. As shown in Table 1,seven clones were monoclonal antibodies specifically reacting with tumor vessel endothelial cells or KMT-17 tumor tissues.

TABLE 1

| Clone No. | Ratio (OD 405–620 nm) Tumor endothelia/ normal endothelia | Immunohistochemical staining of endothelial cells | | |
|---|---|---|---|---|
| | | Tumor tissue | liver | kidney |
| TES1-10-1 | 20.5 | +++ | ++ | ++ |
| TES7-1-7 | 223.0 | – | ND | ND |
| TES17-8-4 | 22.7 | +++ | + | + |
| TES21-14-6 | 23.9 | ++ | + | – |
| TES23-3-10 | 1.9 | +++ | + | – |
| TES26-7-3 | 47.5 | +++ | + | ND |
| TES27-4-4 | 1.0 | +++ | +++ | ND |

ND: not determined.

Selected hybridoma clones were intraperitoneally injected into pristane-primed BALB/c mice and ascites were collected. Then, the antibodies were purified from the ascites of mice by an antibody purification apparatus (Con Sep LC100, Millipore) using protein A affinity chromatography (Millipore).

The reactivity of these monoclonal antibodies to normal vessel endothelial cells and tumor vessel endothelial cells was tested by flow cytometry, which revealed a correlation with the reactivity shown by ELISA.

Subclasses of monoclonal antibodies produced by these hybridomas were determined by ELISA using subclass-specific anti-mouse rabbit antibodies (Zymed). All the 7 antibodies had the subclass of $IgG_1\kappa$.

The hybridomas producing these antibodies were internally deposited on Jan. 31, 1996 at the International Patent Organism Depository (IPOD) in the National Institute of Advanced Industrial Science and Technology (AIST), 1—1, Higashi 1 -Chome, Tsukuba-city, Ibaraki-prefecture, Japan under the accession numbers FERM P-15411 (TES1-10-1), FERM P-15412 (TES7-1-7), FERM P-15413 (TES17-8-4), FERM P-15414 (TES21-14-6), FERM P-15415 (TES23-3-10), FERM P-15416 (TES26-7-3) and FERM P-15417 (TES27-4-4), among which FERM P-15413 (TES17-8-4and FERM P-15415 (TES23-3-10) were transferred to the international deposition on Jan. 16, 1997 under the accession numbers FERM BP-5786 and FERM BP-5787, respectively.

Example 2

Characterization of Tumor Vessel Endothelial Monoclonal Antibodies

In order to examine in vivo accumulation of tumor vessel endothelial antibodies in tumor tissues, $^{125}$I-labeled antibodies were prepared and evaluated for the distribution in organs of rats bearing KMT-17 tumors.

The $^{125}$I-labeled antibodies were prepared by the following procedure. A control antibody or the antibody TES23-3-10 (100 µg) was reacted with $Na^{125}I$ (0.5 mCi) (Amersham) at room temperature for 5 minutes in a vial treated with IODOGEN™ ledegen (2.5 µg) (Pierce), then fractionated in a PD-10 column (Pharmacia) to recover $^{125}$I-labeled protein fractions. The resulting $^{125}$I-labeled antibodies showed a specific radioactivity of 6.0–8.6 µCi/µg.

Subsequently, a mixture of the $^{125}$I-labeled antibody (4.9–6.0 µCi/rat) and unlabeled antibody (99 µg/rat) of each of the control antibody and the antibody TES23-3-10 was intravenously administered to WKAH-Hkm rats (6 week-old, female, Japan SLC) on the 9th day (tumor weight of 1–2 g) after $1 \times 10^6$ KMT-17 cells were subcutaneously transplanted.

On the 8th day after administration, blood, organs (liver, kidney, spleen, small intestine, lung, muscle) and tumor tissue were extracted and determined for radioactivity by a gamma counter (Aloka).

The results are shown in the following Table 2. As apparent from Table 2, the antibody TES23-3-10 accumulated specifically in tumor tissues on the 8th day after administration. However, the control antibody did not show any specific distribution in organs and remained at a too low level to detect.

TABLE 2

| Organs | Tissue/blood distribution ratio |
|---|---|
| Tumor | 4.11 |
| Liver | 0.35 |
| Kidney | 1.24 |
| Lung | 0.24 |
| Spleen | 0.30 |
| Small intestine | 0 |
| Muscle | 0.28 |

Example 3

Analysis of Antigens Recognized by Tumor Vessel Endothelial Monoclonal Antibodies SDS-PAGE and Western blotting were performed according to the following procedure.

Tumor vessel endothelial cells in an amount corresponding to 3 flasks of 75 cm.sup.2 were washed and then incubated with a cytolysis buffer (50 mM Tris-HCl, pH 7.5 containing 1 mM EDTA, 1 mM PMSF, 10 µg/ml aprotinin, 10 µg/ml leupeptin, 1% NONIDET™ P-40 and 150 mM NaCl) at room temperature for 5 minutes. The cells and lysate were collected by a scraper and incubated at 0° C. for 30 minutes. This lysate was centrifuged at 15,000 rpm for 10 minutes, then the protein level in the supernatant was determined.

The supernatant was mixed with an SDS sample solution (2.3 % SDS, 125 mM Tris (pH 6.8), 20% glycerol, 0.05% BPB) in a ratio of 1:1 and boiled for 3 minutes. A protein amount of 1–10 μg was subjected to 4–20% SDS-PAGE followed by Western blotting.

Namely, the blotted nitrocellulose membrane (Millipore) was blocked with skim milk and treated with each antibody (10 μg/ml) dissolved in a TBST solution (25 mM Tris, 150 mM NaCl, 3 m MgKCl , 0.05% TWEEN™ 20) at room temperature for 2 hours. After washed with the TBST solution three times, the membrane was treated with a peroxidase-labeled anti-mouse IgG goat antibody (Zymed) at room temperature for 1 hour and then washed with the TBST solution three times in the same manner.

Then, an X-ray film was exposed to the membrane to detect bands by an ECL Western blotting detection system (Amersham).

As a result, the antibodies TES1-10-1, TES7-1-7, TES17-8-4, TES21-14-6, TES26-7-3 specifically stained a band of a molecular weight of 40 kD, while the antibodies TES23-3-10, TES27-4-4 specifically stained a band of a molecular weight of 80 kD.

FIG. 1 shows the results of detection of 10 μg of antigenic proteins with TES23-3-10 (lane 1) and 1 μg of antigenic proteins with TES1-10-1 (lane 2). The figures on the right indicate molecular weight markers (kD).

Example 4

Effects of Tumor Vessel Endothelial Monoclonal Antibodies on Tumor-transplanted Rats A conjugate (immunoconjugate) of a chemotherapeutic agent neocartinostatin (NCS) and a tumor vessel endothelial monoclonal antibody of the present invention (TES23-3-10) was initially prepared. NCS was linked to the sugar chain at the Fc site of the antibody by using PDPH as a crosslinking agent according to the technique of Zara, J. J. et al., Anal. Biochem. (1991) 194, 156.

The rat sarcoma cell line KMT-17 was intracutaneously transplanted into 5-week old WKAH/Hkm rats (Japan SLC) at a ratio of $5 \times 10^5$ cells/rat. After confirming that the tumor has grown to 6–8 mm square (after 4 days), each of test materials, i.e. PBS as a control (indicated by open circles in FIG. 2), NCS-conjugated antibody TES23-3-10 (5 μg/rat of NCS and 32 μg/rat of the antibody; indicated by solid circles in FIG. 2), the antibody TES23-3-10 (32 μg/rat of the antibody; indicated by open squares in FIG. 2), NCS (5 μg/rat; indicated by solid squares in FIG. 2), or a simple combination of the antibody TES23-3-10 (32 μg/rat of the antibody) and NCS (5 μg/rat) (indicated by open triangles in FIG. 2) was intravenously administered 3 times at intervals of one day (namely, on the days 4, 6 and 8 after transplantation of KMT-17 sarcoma).

The experiment was performed on 5 rats for each group in the same manner. Increase of tumor volume was determined from the 4th day after transplantation of KMT-17 sarcoma to assess antitumor effects on each group. The results are shown in FIG. 2.

Figure 2:
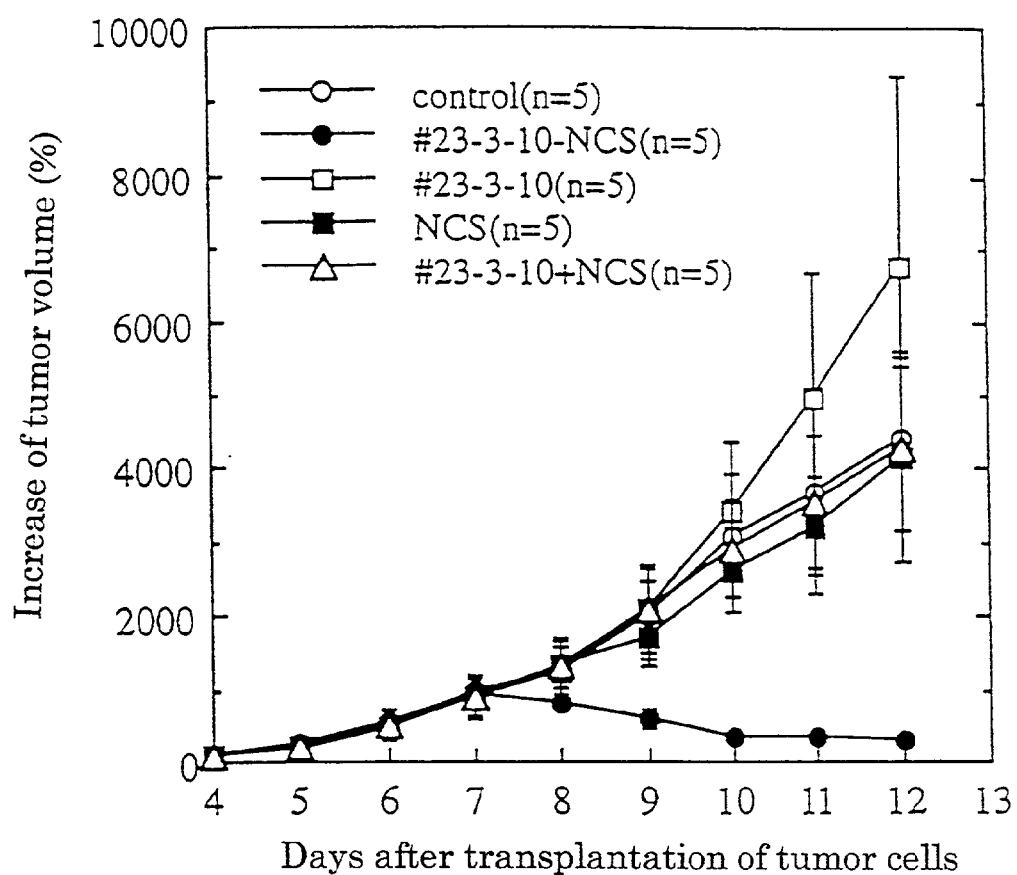
FIG. 2 is a graph showing change in increase of tumor volume when each test material (control, antibody/NCS conjugate, antibody, NCS and a combination of antibody and NCS) was administered to rats bearing cancer cells transplanted.

As shown in FIG. 2, the group treated with NCS-conjugated antibody TES23-3-10 showed a significant inhibitory effect on proliferation of transplanted rat solid cancers.

In order to examine antitumor effects based on antibody-dependent cytotoxic activity, antibodies were administered alone. Namely, $1 \times 10^6$ cells/rat of the rat sarcoma cell line KMT-17 were subcutaneously transplanted into 7-week old WKAH/Hkm rats (Japan SLC). After confirming that the tumor has grown to 6–8 mm square (after 4 days), 1 mg/rat of the antibody TES23-3-10 or a control antibody was intravenously administered 5 times daily.

The experiment was performed on 7 rats for each group in the same manner. Increase of tumor volume was determined from the 4th day after transplantation of KMT-17 sarcoma to assess antitumor effects on each group. The results are shown in FIG. 3.

Figure 3:
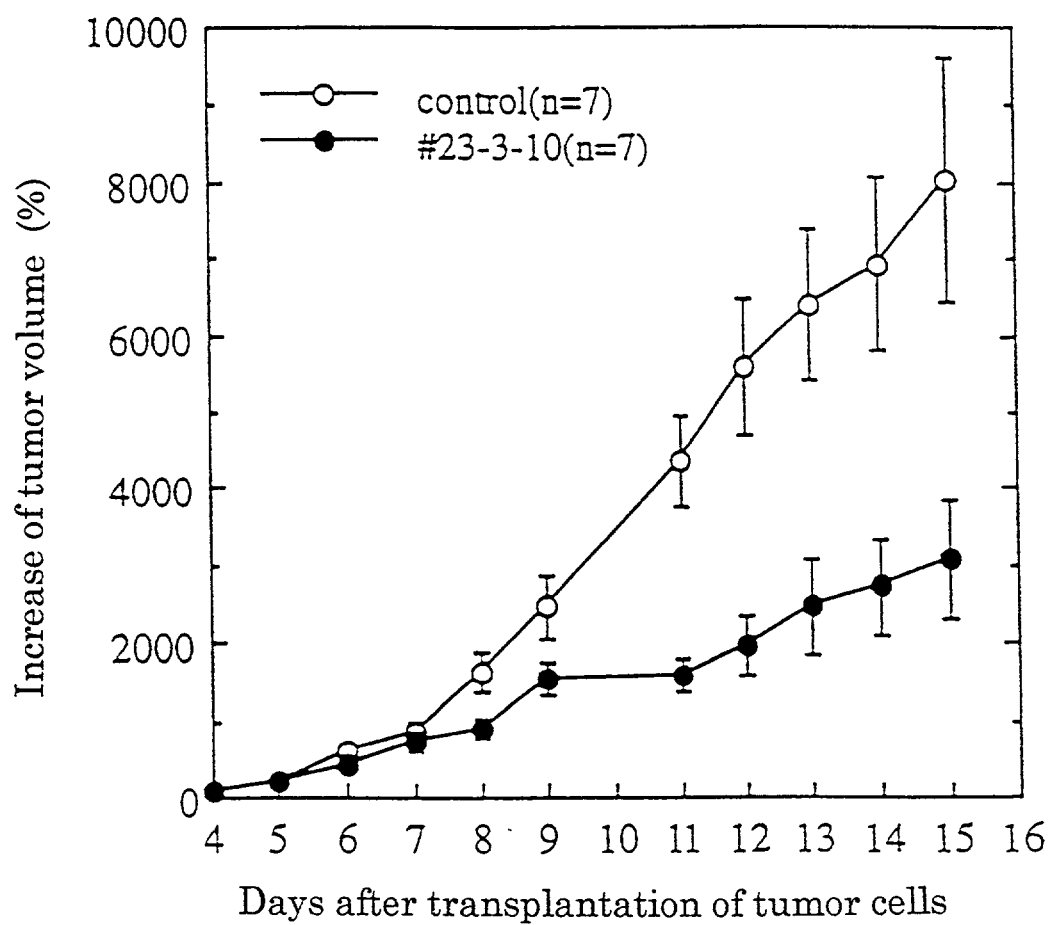
FIG. 3 is a graph showing change in increase of tumor volume when each test material (control and antibody) was administered to rats bearing cancer cells transplanted.

As shown in FIG. 3, the group treated with the antibody TES23-3-10 showed a significant inhibitory effect on proliferation of transplanted rat solid cancers.

Example 5

Specific Antiproliferative Effects of Tumor Vessel Endothelial Monoclonal Antibodies on Tumor Vessel Endothelial Cells A conjugate (immunotoxin) of pokeweed seed-derived anti-virus protein (PAPS) described in Barbieri, L. et al., Biochem. J. (1982) 203, 55–59 (Inland Laboratories) and a tumor vessel endothelial monoclonal antibody of the present invention (TES23-3-10 or TES17-8-4) was prepared. In the same manner, a conjugate of PAPS and a control antibody (MOPC-31 C) was prepared. After PAPS was conjugated to each antibody by using SMPT (Pierce) as a crosslinking agent on the antibody side by the method of Thrope, P. E. et al., Cancer Res. (1987) 47, 5924–5931 and 21T (Pierce) as a crosslinking agent on the PAPS side similarly by the method of Thrope, P. E. et al., Cancer Res. (1987) 47, 5924–5931, the PAPS-conjugated antibody was purified by gel filtration on SUPERDEX™ 200 HR 10/30 column (Pharmacia Biotech).

Isolated tumor vessel endothelial cells or normal vessel endothelial cells were plated on a 96-well plate (Falcon) at a ratio of $2 \times 10^3$ cells/well and incubated for 6–8 hours. After confirming that the cells have been attached, the plate was incubated for 70.5 hours with PAPS at a final concentration of 1 μM-0.1 nM (indicated by open rhombuses in FIGS. 4 and 5), or PAPS-conjugated control antibody MOPC-31 C (indicated by open circles in FIGS. 4 and 5), PAPS-conjugated antibody TES23-3-10 (indicated by open triangles in FIGS. 4 and 5) or PAPS-conjugated antibody TES17-8-4 (indicated by open squares in FIGS. 4 and 5) each at a final concentration of 10 nM-10 pM. Then, the plate was incubated for further 90 minutes with 20 μl/well of CELLTITER 96 ™ Aqueous Assay Reagents (Promega).

After the reaction was stopped by adding 25 μl/well of 10% SDS, the absorbance was measured at 492–690 nm (measured at 492 nm vs. reference wavelength of 690 nm) using a microplate reader (Labsystems). Antiproliferative activity was calculated on the basis of the absorbance of the control (grown on the medium alone) assumed as 100%. The results are shown in FIGS. 4 and 5.

Figure 4:
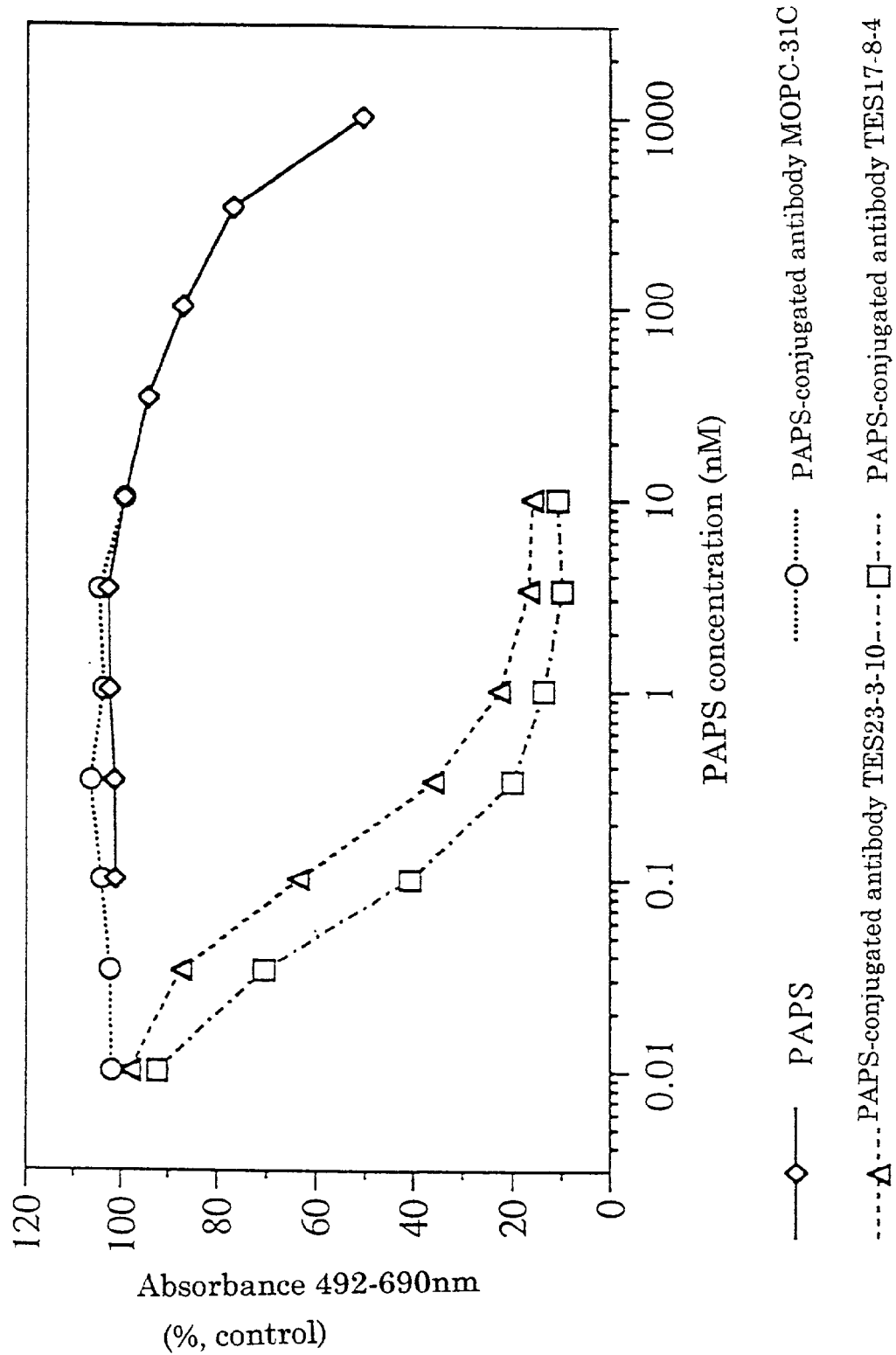
FIG. 4 is a graph showing antiproliferative effects of PAPS, PAPS-conjugated control antibody MOPC-31C, PAPS-conjugated antibody TES23-3-10 and PAPS-conjugated antibody TES17-8-4 on tumor vessel endothelial cells.
Figure 5:
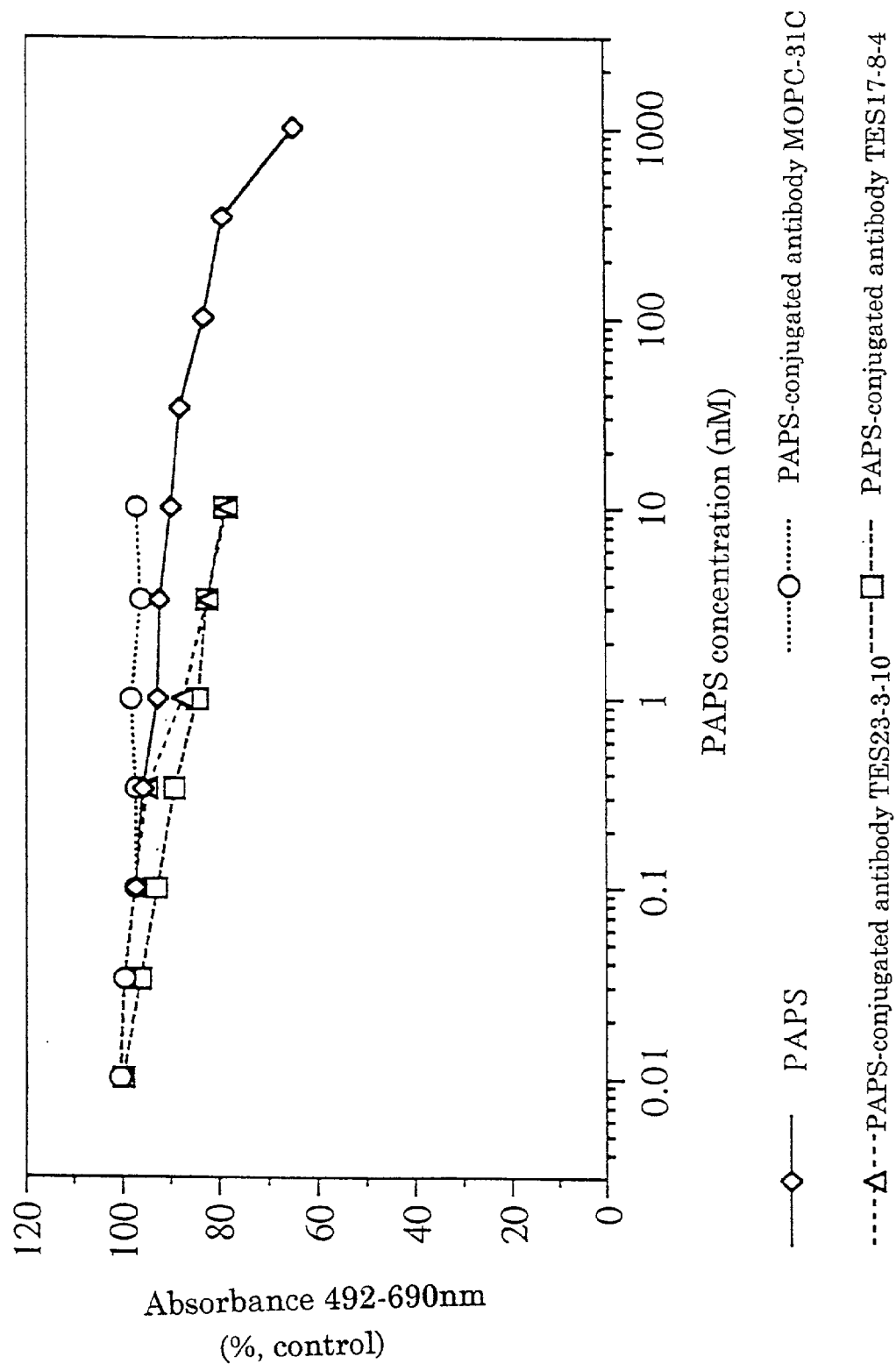
FIG. 5 is a graph showing antiproliferative effects of PAPS, PAPS-conjugated control antibody MOPC-31C, PAPS-conjugated antibody TES23-3-10 and PAPS-conjugated antibody TES17-8-4 on normal vessel endothelial cells.

As shown in FIGS. 4 and 5, PAPS-conjugated antibody TES23-3-10 or PAPS-conjugated antibody TES17-8-4 showed a strong antiproliferative effect on tumor vessel endothelial cells, but no effect on normal vessel endothelial cells. PAPS-conjugated control antibody MOPC-31C did not show any antiproliferative effect even at 10 nM on both of tumor vessel endothelial cells and normal vessel endothelial cells.

INDUSTRIAL APPLICABILITY

Monoclonal antibodies of the present invention, which can recognize antigens existing on the surface of tumor vessel endothelial cells, are useful alone or in combination with conjugating molecules such as chemotherapeutic agents or radioisotopes, as pharmaceutical or diagnostic agents, particularly for the treatment or diagnosis of tumors.

What is claimed is:

1. A monoclonal antibody which recognizes an antigen having a molecular weight of 80 kD on the surface of tumor vessel endothelial cells, and having a binding affinity for tumor vessel endothelial cells equivalent to or greater than the binding affinity for normal vessel endothelial cells as measured by ELISA, wherein:
   the antigen having the molecular weight of 80 kD is present on the surface of endothelial cells in liver tissue and spleen tissue, and
   the molecular weight of the antigen is determined by non-denaturing SDS-PAGE,
   and the monoclonal antibody is selected from the group consisting of:
   (a) an antibody produced by a hybridoma bearing the accession number FERM BP-5787;
   (b) a chimeric antibody comprising the variable regions of an antibody produced by said hybridoma; and
   (c) a reshaped human antibody comprising the complementarity determining regions of an antibody produced by said hybridoma.

2. The monoclonal antibody according to claim 1 further characterized as binding equally or more strongly with endothelial cells in tumor tissues relative to endothelial cells in liver tissue and to endothelial cells in kidney tissue as measured by immtinohistochemical staining.

3. The monoclonal antibody according to claim 1, wherein the ratio of the affinity for tumor vessel endothelial cells relative to normal vessel endothelial cells is 1.9 to 200 or more.

4. The monoclonal antibody according to claim 1, further characterized as having an organ tissue/blood distribution ratio wherein the distribution level in tumor tissues is equivalent to or higher than the level in blood, liver, lung, spleen, small intestine or muscle.

5. The monoclonal antibody according to claim 4 wherein the distribution level in the tumor tissues relative to that in blood is in a ratio of 4 or more.

6. The monoclonal antibody according to claim 5 wherein the distribution level in tumor tissues relative to that in the liver, lung, spleen, small intestine or muscle is in a ratio of 10 or more.

7. The monoclonal antibody according to claim 1 further characterized as having anti-tumor activity.

8. The monoclonal antibody according to claim 7, wherein the anti-tumor activity is an antibody dependent cytotoxic activity.

9. The monoclonal antibody according to claim 7, wherein the anti-tumor activity is an antiproliferative activity.

10. A pharmaceutical composition comprising the monoclonal antibody according to claim 1 and a pharmaceutically acceptable carrier or diluent.

11. The pharmaceutical composition according to claim 10, wherein the composition is in a form suitable for intravenous administration.

12. A pharmaceutical or diagnostic composition comprising a conjugate of (a) the monoclonal antibody according to claim 1 and (b) a conjugating molecule selected from the group consisting of anticancer chemotherapeutic agents, radioisotopes, proteinaceous toxins, lethal proteins, enzymes and streptavidin.

13. The pharmaceutical or diagnostic composition according to claim 12 in kit form.

14. A diagnostic composition comprising a monoclonal antibody according to claim 1.

15. The monoclonal antibody of claim 1, wherein the monoclonal antibody is produced by a hybridoma bearing the accession number FERM BP-5787.

16. A chimeric antibody comprising the variable regions of an antibody produced by a hybridoma bearing the accession number FERM BP-5787.

17. A reshaped human antibody comprising the complementarity determining regions of an antibody produced by a hybridoma bearing the accession number FERM BP-5787.

* * * * *